United States Patent
Armbruster et al.

(10) Patent No.: US 10,317,419 B2
(45) Date of Patent: Jun. 11, 2019

(54) MEANS AND METHODS OF MEASURING PARATHYROID HORMONE IN PATIENTS SUFFERING FROM OXIDATIVE STRESS

(71) Applicant: Immundiagnostik AG, Bensheim (DE)

(72) Inventors: Franz Paul Armbruster, Bensheim (DE); Berthold Hocher, Kleinmachnow (DE); Hans Juergen Groen, Bensheim (DE); Heinz Juergen Roth, Heidelberg (DE)

(73) Assignee: Immundiagnostik AG, Bensheim (DE)

( * ) Notice: Subject to any disclaimer, the term of this patent is extended or adjusted under 35 U.S.C. 154(b) by 111 days.

(21) Appl. No.: 14/380,147

(22) PCT Filed: Feb. 22, 2013

(86) PCT No.: PCT/EP2013/053632
§ 371 (c)(1),
(2) Date: Aug. 21, 2014

(87) PCT Pub. No.: WO2013/124462
PCT Pub. Date: Aug. 29, 2013

(65) Prior Publication Data
US 2015/0017738 A1 Jan. 15, 2015

(30) Foreign Application Priority Data
Feb. 22, 2012 (EP) .................... 12156441

(51) Int. Cl.
*G01N 33/53* (2006.01)
*G01N 33/78* (2006.01)
*C07K 16/26* (2006.01)
*G01N 33/68* (2006.01)

(52) U.S. Cl.
CPC ............ *G01N 33/78* (2013.01); *C07K 16/26* (2013.01); *G01N 33/6848* (2013.01); *G01N 33/6854* (2013.01); *G01N 33/6893* (2013.01); *C07K 2317/30* (2013.01); *C07K 2317/34* (2013.01); *G01N 2333/635* (2013.01); *G01N 2500/00* (2013.01); *G01N 2800/046* (2013.01); *G01N 2800/347* (2013.01); *G01N 2800/7009* (2013.01)

(58) Field of Classification Search
CPC ............... C07K 16/26; C07K 2317/34; G01N 2333/635; G01N 33/78; G01N 33/6893; G01N 2800/347; G01N 2500/00; G01N 2800/04; G01N 2800/046; G01N 2800/7009; G01N 33/6848; G01N 33/6854
See application file for complete search history.

(56) References Cited

U.S. PATENT DOCUMENTS

| 2005/0095236 A1* | 5/2005 | Zahradnik | C07K 16/26 424/130.1 |
| 2006/0062783 A1* | 3/2006 | Roskos | C07K 16/26 424/141.1 |
| 2006/0211054 A1* | 9/2006 | Armbruster | G01N 33/74 435/7.5 |
| 2007/0098726 A1 | 5/2007 | Cantor et al. | |

FOREIGN PATENT DOCUMENTS

| WO | WO 02/082092 A2 | 10/2002 |
| WO | WO 03/003986 A2 | 1/2003 |

OTHER PUBLICATIONS

Van Regenmortel, A Companion to Methods of Enzymology 9:465-472.*
Brown et al (J. Immuno. May 1996, 3285-91.*
Vajdos et al. (J. Mol. Biol. Jul. 5, 2002, 320(2):415-28.*
Rudikoff et al. (PNAS USA (1982) 79:1979-1983).*
Logue et al., J. Immunological methods, 1991. 137, 159-166.*
Lopez et al (Clinical Chemistry, 2010, 56:2 p. 281-290.*
S. Tomasello, "Secondary Hyperparathyroidism and Chronic Kidney Disease", Diabetes Spectrum, vol. 21, No. 1, 2008, pp. 19-25.
B. Hocher et al., "Measuring Parathyroid Hormone (PTH) in Patients with Oxidative Stress—Do We Need a Fourth Generation Parathyroid Hormone Assay?", PLOS ONE Public Library of Science, vol. 7, No. 7, Jul. 6, 2012, pp. 1-10.

* cited by examiner

*Primary Examiner* — Julie Wu
*Assistant Examiner* — Carmencita M Belei
(74) *Attorney, Agent, or Firm* — Blank Rome LLP

(57) ABSTRACT

A method is disclosed for obtaining an antibody or antibody fragment to a conformational epitope specific for misfolded inactive human parathyroid hormone and fragments thereof. The method includes the steps of a) immunizing an animal with an immunogen which comprises oxidized parathyroid hormone or an oxidized fragment of parathyroid hormone, or both; and b) recovering an antibody, antibody fragments, or single chain antibody. The complementary determining region of the recovered antibody, antibody fragment or single chain antibody is capable of specifically recognizing a conformational epitope (antigenic determinant) which is present on oxidized parathyroid hormone and fragments thereof only but not regular bioactive human parathyroid hormone.

9 Claims, 11 Drawing Sheets
Specification includes a Sequence Listing.

Methionine → Methionine Sulfoxide → Methionine Sulfone

MEANS AND METHODS OF MEASURING PARATHYROID HORMONE IN PATIENTS SUFFERING FROM OXIDATIVE STRESS

FIELD OF THE INVENTION

The invention relates to means and methods of measuring parathyroid hormone in samples of body fluid.

BACKGROUND OF THE INVENTION

The parathyroid hormone (PTH) is formed in the parathyroid gland (Glandulae parathyroideae) and secreted into the blood circulation. In the intact form it consists of a single polypeptide chain having 84 amino acids and a molecular weight of ca. 9500 Dalton (see SWISS-PROT:P01270, PTHY-HUMAN showing the amino acid sequence MIPAKDMAKV MIVMLAICFL TKSDGKSVKK RSVSEIQLMH NLGKHLNSME RVEWLRKKLQ DVHNFVALGA PLAPRDAGSQ RPRKKEDNVL VESHEKSLGE ADKADVNVLT KAKSQ) (SEQ ID NO:1). Together with vitamin-D and calcitonin it brings about the mobilization of calcium and phosphate out of the bone skeleton and increases the uptake of calcium in the intestines and the excretion of phosphate via the kidneys. The concentration of biologically active PTH peptides in plasma or serum is thus an important diagnostic parameter for determining presence and degree of hyper- or hypo-parathyroidism; for a quantification of osteoblast and/or osteoclast activity; a treatment with vitamin-D and vitamin-D metabolites; an estimation of the presence of aluminum or a possible oestrogen deficiency in post-menopausal dialysis patients; for determining the steroid or cyclosporine dosage after kidney transplantations or a treatment or prevention of pathological bone marrow changes, uraemic conditions and chronic kidney failure.

Secondary hyper-parathyroidism further occurs frequently in chronic kidney disease as an adaptive response to deteriorating renal function. This is because circulating 1,25-dihydroxy vitamin D starts to decrease very early in stage 2 of chronic kidney disease and continues to fall as the glomerular filtration rate (GFR) decreases further, and the renal 1α-hydroxylase is inhibited by hyperphosphatemia, hyper-uricemia, metabolic acidosis as well as 25-hydroxyvitamin D deficiency. As GFR decreases below 60 mL/min/1.73 m$^2$ phosphate is retained which stimulates secretion of PTH. Hypocalcaemia develops as the GFR decreases below 50 mL/min/1.73 m$^2$, further stimulating a release of PTH. With disease progression, intact PTH (aa 1-84) half-life increases and C-terminal fragments of the hormone accumulate in serum. A relative state of end-organ resistance to the hormone exists but chronic elevation of it has major consequences resulting in bone loss, particularly of cortical bone, fractures, vascular calcification, cardiovascular disease, and hence an increased cardiovascular mortality (cf Fraser W D, *Hyperparathyroidism*. Lancet 2009; 374:145f) A reliable method of determining the concentration of biologically active PTH peptides in serum is therefore key for detecting patients with hyperparathyroidism as well as for subsequent monitoring of therapeutic interventions.

The first generation of immunoassays for measuring PTH in serum were based on radiolabeled bovine PTH peptides and polyclonal antisera against parathyroid hormone (Berson S A et al. Proc Natl Acad Sci USA. 1963; 49:613-617). As the biologic activity is located in the amino-terminal portion of the PTH peptide and the PTH peptide following its secretion into circulation degraded within minutes in active and inactive fragments, the radioimmunoassay were also detecting inactive degradation products. The first generation of PTH assays therefore produced no reliable clinical measurements since the sera of patients with a renal failure contain high concentrations of inactive PTH fragments.

The second generation of immunoassays uses two antibodies, one binding in the amino-terminal portion of the PTH peptide with the biologic activity and the other in its C-terminal portion. The characterising with synthetic fragments showed however that these immunoassays also determined an inactive large PTH (aa 7-84) fragment (John M R et al. (1999), J. Clin. Endocrinol. Metab., 84. 4287-4290; Gao P et al. 2000, Poster M455, ASBMR 22nd Annual Meeting; Roth H J et al. (2000), Poster P1288; 11th International Congress of Endocrinology, Sydney). This co-determination of the inactive large PTH fragment (7-84) was made responsible for the discrepancy between measured PTH concentrations and clinical findings as the large PTH fragment is likely competing with intact PTH peptides for the binding site of the PTH receptor.

A third generation PTH assay has been developed to overcome the problems with inactive large PTH fragments, which however fails to improve the diagnosis of bone diseases or other clinical signs of secondary hyperparathyroidism in uraemic patients (Brossard J H et al., *Influence of glomerular filtration rate on non-(1-84) parathyroid hormone (PTH) detected by intact PTH assays*, Clin Chem. 2000; 46:697-703). There have been speculations about systematic errors in the determination or a PTH resistance of osteoblasts or a genetically reduced expression of PTH receptor.

In summary, it is generally accepted in the field that the parathyroid hormone is cleaved in liver, kidney and circulation within minutes into active and inactive fragments and that some fragments have a biological activity comparable with intact PTH peptides whereas others such as hPTH (3-34) seem to inhibit the effects of parathyroid hormone (see EP-A 0 349 545; Schmidt-Gayk et al. (1999) Osteologie forum, 5, 48-58), Suva et al. (1987) Science, 237, 893ff; EP 0 451 867). Moreover, that large PTH non-(1-84) fragments may lead to erroneous determinations (LePage R. et al. (1998) Clin. Chem., 44, 805-809). The term "large PTH fragment" has been coined for PTH fragments which lack amino acid residues at the amino-terminus but which are detected by 2nd generation PTH assays. Additionally, dipeptidyl peptidase-4 (DPP4) is expressed on the surface of many cell types and a rather indiscriminate serine exopeptidase. This led to the hypothesis of PTH further being in vivo a substrate of DPP4 or a similar exoproteinase. Consequently, a two-site immunoassay has been developed employing antibodies that can distinguish between biologically active and biologically inactive PTH peptides that are missing the utmost 2 amino-terminal amino acids (see WO 2001/44818 (Armbruster et al), WO 96/10041 (Mageriein et al); WO 2003/03986 (Hutchison J S)).

However, it was found that serum samples of uraemic patients may contain intact PTH polypeptide chains which are inactive because oxidized at one of its methionines. Such kind of oxidation seems to be particularly relevant for dialysis patients whose blood plasma is exposed to oxidative stress. This led to the development of an immunoassay for determination of non-oxidized PTH (aa 1-84) and biologically active fragments thereof (WO 2002/082092). Notwithstanding, it needs to be ascertained why uraemic patients with normal bone transformation sometimes have serum levels of intact PTH which are more than 2.5 higher than in patients with healthy kidneys (pathological limit in the case of patients with healthy kidneys: 65 µg PTH/L; for patients having uraemic conditions: 165 µg PTH/L serum). Further, uraemic patients with relatively high PTH values often manifest significant differences in bone transformation (Slatopolsky E et al. (2000), Kidney Int., 58, 753-761). Thus these patients often have in the serum eight to ten times increased PTH concentrations, but low normal values for bone specific alkaline phosphatase (ostase). These patients seem to free from symptoms of an excessive PTH activity.

The state of the art therefore still represents a problem. It is further an object of the invention to make available a fast and reliable method for the determination of active parathyroid hormone in a sample of a body fluid, which method particularly allows an early detection of a deteriorating renal function.

SUMMARY OF THE INVENTION

This problem is solved by a method for obtaining an antibody or antibody fragment to a conformational epitope specific for misfolded inactive human parathyroid hormone and fragments thereof, comprising the steps of a) immunizing an animal with an immunogen which comprises oxidized parathyroid hormone or a oxidized fragment of parathyroid hormone, or both; and b) recovering antibodies; whereby the complementary determining region of the antibody or antibody fragment or single chain antibody specifically recognizes a conformational epitope (antigenic determinant) which is present on oxidized parathyroid hormone and fragments thereof only but not regular bioactive human parathyroid hormone.

The disclosure further relates to a complementary determining region recognizing a conformational epitope presented by human parathyroid hormone or a fragment thereof comprising at positions 8, 18 or both methionine R-sulfoxide, methionine L-sulfoxide or methionine sulfone. The complementary determining region may also recognize a conformational epitope of a human parathyroid hormone or a fragment thereof comprising at position 23 oxidized tryptophan and/or lacking the utmost aminoterminal amino acids at positions 1 and 2 or both. To be clear it is the human parathyroid hormone or fragment thereof which comprises in its amino acid sequence at positions 8, 18 or 23 oxidized amino acids. This does not mean that the conformational epitope is made up of a primary structure comprising any one of these oxidized amino acids but the conformational epitope is a tertiary structure formed by the oxidized PTH sequence which has flipped into an alternative tertiary structure and the conformational epitope is a characteristic portion of that alternative tertiary structure for which reason the respective antibody or antibody fragment recognizes all types of oxidized or misfolded PTH structures.

The disclosed antibody may be a monoclonal mouse or rat antibody. The preferred immunogen for challenge, preferably given with incomplete Freund's (mineral oil only), is a carrier protein having bound as hapten any one of synthetic oxidized human parathyroid hormone, synthetic oxidized fragment of human parathyroid hormone or synthetic oxidized peptide comprising the amino acid sequence 1 to 38 of human parathyroid hormone or a substantial portion, fragment or variant thereof. The antibodies elicited by this challenge may be isolated or screened by affinity chromatography using fragments of synthetic oxidized human parathyroid hormone linked to a solid phase or a marker molecule. The screening or isolation of the antibody is done using a conformational epitope which is made up by the oxidized human parathyroid hormone or a fragment thereof, preferably comprising the amino acid sequence 3 to 34 wherein the methionine at position 8 is likely first oxidized.

A further aspect of the disclosure relates to a binding material for removing oxidized human parathyroid hormone from a sample such as a serum sample of a patient on dialysis, which binding material comprises bound to a solid phase antibodies or antibody fragments or single-chain antibody fragments as disclosed above. The binding material may be in the form of a slurry, preferably a slurry of Sepharose beads having covalently linked a conformational antibody for oxidized PTH and fragments thereof.

Another aspect of the disclosure relates to a method of measuring the concentration of human parathyroid hormone in a sample of a body fluid, comprising the step of contacting the sample with a solid phase or slurry as described comprising antibodies recognizing oxidized parathyroid hormone, and measuring the concentration of parathyroid hormone in the flow-through or supernatant.

This method of measuring the concentration of human parathyroid hormone in a sample of a body fluid may comprise the step of measuring the concentration of parathyroid hormone by a two-site immunoassay wherein one antibody binds in the aminoterminal portion with amino acids 1 to 34 of the parathyroid hormone.

The disclosure further encompasses a method of measuring the concentration of human parathyroid hormone in a sample, comprising the step of measuring the concentration of parathyroid hormone fragments by tandem mass spectroscopy, optionally preceded by modern liquid chromatography.

Another aspect of the disclosure concerns the use of a binding material or antibodies or method as described in any preceding claim in a method of diagnosis, notably for determining in vitro secondary hyperparathyroidism, kidney failure or both.

BRIEF DESCRIPTION OF THE DRAWINGS

The present invention is best understood when read in conjunction with the accompanying tables and figures, which serve to illustrate the preferred embodiments. It is understood, however, that the invention is not limited to the specific embodiments disclosed in the figures.

DETAILED DESCRIPTION OF THE INVENTION

Figure 1A:
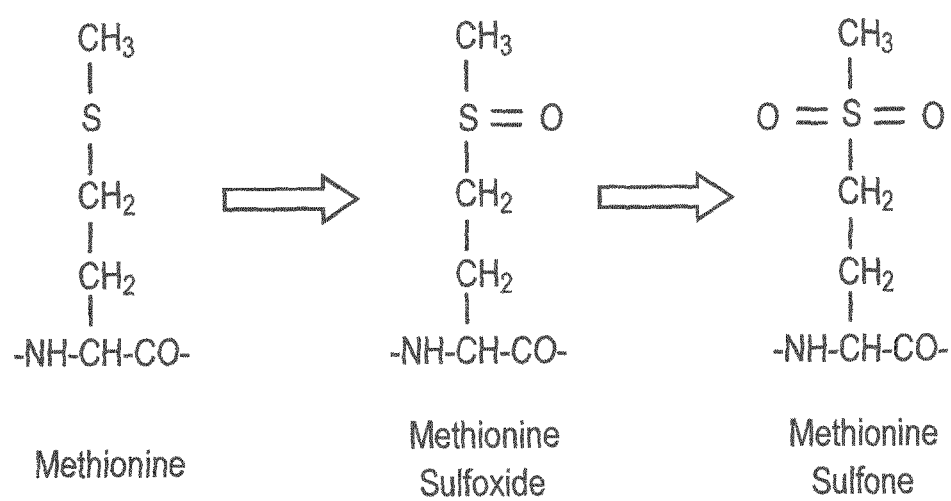
FIG. 1A shows the formulae of methionine and its oxidized forms methionine sulfoxide and methionine sulfone. There are two methionines at positions 8 and 18 in the polypeptide chain of mature PTH.

The oxidation of parathyroid hormone (PTH) peptide at methionine residues 8 and/or 18 results in a loss of biological activity. (Galceran T et al., *Absence of biological effects of oxidized parathyroid hormone-(1-34) in dogs and rats*. Endocrinology 1984; 115(6):2375-2378. Horiuchi N et al., *Effects of oxidation of human parathyroid hormone on its biological activity in continuously infused, thympamthymidectomized rats*, J Bone Miner Res 1988; 3(3):353-358. Zull J E et al., *Effect of methionine oxidation and deletion of ammo-terminal residues on the conformation of parathyroid homone. Circular dichroism studies*. J Biol Chem 1990; 265(10):5671-5676). Thus, studies by independent groups have shown that the oxidation of PTH diminishes its interaction with the respective receptor and that oxidized PTH peptides cannot stimulate the PTH receptor to generate cAMP, the second messenger of PTH. WO 2002/082092 (Roth H J et al) discloses a two-site immunoassay which can distinguish between oxidized PTH and "bioactive PTH" and wherein masking antibodies are added which bind to oxidized methionine 8 or 18 so that an antibody of the two-site immunoassay can no longer binding to a nearby site comprising the parathyroid receptor binding domain due to steric hindrances. Further studies showed that such masking antibodies must overcome with the immunological problem that the oxidation of methionine gives rise to two different stereoisomers, methionine S-sulfoxide (Met-S—O) and methionine R-sulfoxide (Met-R—O) with the sulfur being a chiral center, or even methionine sulfone (MetO2) so that such antibodies must bind to a plethora of primary structures, in addition to the problem that a multiplicity of reactive oxygen species (ROS) are possibly involved in the oxidation of the parathyroid hormone.

Methionine sulfoxide oxidation is inhibited in vivo by lower molecular weight antioxidants (LMWA) such as glutathion, histidin dipeptide, uric acid, bilirubin, ascorbic acid or tocopherol. Once PTH has been oxidized comprising a Met-S—O and Met-R—O the endogenous methionine sulfoxide reductase type A (MRSA) can reduce Met-S—O only but not Met-R—O. Whether there is a methionine sulfoxide epimerase or other routes for reducing the Met-R—O stereoisomer remains to be shown. Thus, the oxidation of PTH is only partly reversible, depending whether the oxidation resulted in Met-S—O, Met-R—O or MetO$_2$. The oxidation to MetO$_2$ however is not reversible. It was however found by the present inventors that any methionine oxidation of PTH impacts its folding and tertiary structure as oxidized methionines are less hydrophobic and more polar. This may explain why intact PTH assays conventionally used in clinical practice poorly reflect PTH-related bone and cardiovascular abnormalities.

The present disclosure provides a fast and reliable method to remove all forms of oxidized or misfolded PTH polypeptides from serum or plasma samples, say all PTH molecules which have taken on a new tertiary structure due to oxidative stress and/or methionine oxidation. The present disclosure provides a method for measuring the amount or concentration of correctly folded bioactive PTH molecules in a serum sample which is particularly important for patients on dialysis. In the examples below, we used the herein disclosed method and assay strategy in a patient population known to be exposed to oxidative stress: end-stage: renal disease patients on intermittent hemodialysis (Witko-Sarsat V et al, *Advanced oxidation protein products as a novel marker of oxidative stress in uremia*. Kidney Int. 1996 May; 49(5): 1304-13). The present disclosure demonstrates that established ways of measuring PTH generally result in too high plasma concentrations of active PTH as compared to results considering the folding and oxidation status of PTH. Moreover, the correlation proved to be very weak between conventional PTH measurements and measurements after removal of all oxidized and misfolded PTH polypeptide chains.

The present disclosure further provides an antibody for a common conformational epitope which is specific for all forms of oxidized parathyroid hormone and fragments thereof, at least comprising the amino acid sequence from 3 to 34 of parathyroid hormone and being biologically inactive. This definition shall encompass all forms of oxidized human parathyroid hormone, particularly oxPTH(aa 1-84), oxPTH(aa 1-52), oxPTH(aa 1-34), oxPTH(1-36), oxPTH(aa 1-37), oxPTH(1-38), oxPTH(aa 3-84), oxPTH(aa 3-38) etc. The conformational epitope specific for misfolded and/or oxidized human parathyroid hormone is therefore composed of structures present in the aminoterminal portion of parathyroid hormone. All oxidized forms of the human parathyroid hormone seem to be inactive and misfolded. Thus, the disclosure comprises the information that the aminoterminal portion of the human parathyroid hormone can flip into an alternative tertiary conformation which is biologically inactive. The alternative conformation flip can likely be brought about too by a deletion of the second utmost or more (6) amino acids at the aminoterminus or by an oxidation of the methionine residues at positions 8, 18 or both, which oxidations make the hydrophobic side chain of methionine more polar and hydrophilic, or even by an oxidation of tryptophan at position 23. Due to the low amounts of parathyroid hormone in serum, it is however completely unclear which of those "degradation or inactivation mechanisms" are physiologically more relevant, in other words, it remains to be examined whether the "large PTH fragments" in serum are degradation products of previously oxidized parathyroid hormone or vice versa, and whether the oxidation points to a biological mechanism for inactivation.

The present disclosure also relates to a method for obtaining an antibody which specifically binds to a conformational epitope or antigenic determinant of inactivated, misfolded or oxidized human parathyroid hormone. The disclosure further provides a reagent for removal of inactivated, misfolded or oxidized human parathyroid hormone from body fluids such as serum, plasma or whole blood. A preferred embodiment relates to a column material with a covalently linked antibody recognizing a conformational epitope specific for inactive, oxidized and/or misfolded parathyroid hormone or fragments thereof, comprising at least amino acids 3 to 34 of PTH. The disclosure provides an antibody which does not recognize biologically active hPTH(aa 1-84) or biologically active fragments thereof, but only inactive PTH peptides which are such modified or oxidized at any one position in the aminoterminal portion 1 to 38 of the parathyroid hormone so that this portion flips into another tertiary conformation in which it is inactive and cannot bind to its receptor.

The disclosure thus provides methods and means for measuring the active parathyroid hormone concentration in serum or plasma of patients, notably patients on dialysis and subject to reactive oxygen species (ROS) and oxidative stress.

EXAMPLES

Example 1

Oxidation of hPTH(aa 1-84)

200 human PTH(1-84) purchased from Bachem AG (Bubendorf, Switzerland) was dissolved in 400 µl of 0.1 M acetic acid (final concentration of 0.5 µg/µl), mixed 1:1 with 30% hydrogen peroxide and incubated for 45 min at 37° C. to obtain a mixture of PTH(1-84) peptides oxidized at methionines 8, 18, and both. Afterwards, the mixture was cooled on ice, divided into aliquots and lyophilized.

Oxidation of hPTH(aa 1-38) Conjugate

Human PTH(aa 1-38) peptide (Art.No. A1105AG.1, Immundiagnostik AG, Bensheim, Germany) was coupled to bovine thyreoglobulin by the carbodiimide method, dissolved in 1.0 ml 0.1% acetate buffer, pH 5.0, mixed 1:1 with 30% hydrogen peroxide and incubated for 18 hours at 37° C. to obtain oxPTH(aa 1-38) conjugate.

Oxidation of Biotin-hPTH(ae 1-38)

Human PTH(aa 1-38) peptide (Art. No. A1105AG.1, Immundiagnostik AG, Bensheim, Germany) was dissolved in 1.0 ml 0.1% acetate buffer, pH 5.0, mixed 1:1 with 30% hydrogen peroxide and incubated for two hours at 37° C. to obtain oxPTH(aa 1-38) peptides. Following lyophilisation, the oxPTH(aa 1-38) was conjugated to biotin using water-soluble biotin-sulfosuccinimidyl ester.

Example 2

Monoclonal Antibodies Against a Conformation Epitope of Oxidized PTH(aa 1-38)

Monoclonal antibodies were raised in BALB/c-mice. The mice were immunized with the oxPTH(aa 1-38) thyreoglobulin conjugate at 200 µg for both primary and secondary immunizations with incomplete Freund's (mineral oil only) in the intraperitoneal cavity. Each of the antisera was tested for binding to non-oxidized biotin-hPTH(1-38). To detect antibodies specifically recognizing oxPTH(aa 1-38) peptides, we used the double antibody separation technique and as tracer biotin-oxPTH(aa1-38) labelled with 125I-streptavidin. After cell fusion and HAT selection, selected hybridomas were screened in the same way, namely for binding to human oxidized PTH(aa 1-84) but not to human PTH(aa 1-84).

For ultimate characterization of the specificity of the monoclonal antibodies (MAB) and for identification of a monoclonal antibody recognizing a conformation epitope common to oxidized hPTH(aa 1-38) peptides, say common to all forms of oxidized hPTH(aa 1-38) independently from oxidation status and chirality (Met-R—O, Met-S—O, and MetO$_2$ at positions 8, 18 and both), the antibody was immobilized on CNBr-activated Sepharose 4B (GE Healthcare Bio-Sciences, Uppsala, Sweden). Hundred µl aliquot of the slurry was filled in a column (MobiSpinColumn, MoBiTec, Göttingen, Germany) and equilibrated with PBS buffer, pH 7.4. Then 2.5 µg of lyophilized oxidized hPTH (1-84) were dissolved in 300 µl of equilibrating buffer and applied on the column. The column was incubated end-over-end for 1 h at room temperature, washed with 300 µl of equilibrating buffer, followed by 3 washes with 300 µl of distilled water, and then eluted 2 times with 200 µl of elution buffer (0.1% TFA). Flow-through, wash fractions (equilibrating buffer and water) as well as eluate of the column were collected separately, lyophilized and analyzed by nanoLC-ESI-FT-MS. Since oxidized hPTH(aa1-38) regularly results in a variety of oxidized PTH fragments, oxidized at positions 8, 18 or both, an antibody or antibody clone can be selected which binds oxidized parathyroid hormone independently from the specific type of protein oxidation. Consequently, a monoclonal antibody ("oxPTH-ConforMAB") recognizing a conformation epitope present on all forms of oxidized hPTH(aa 1-84) and fragments thereof was selected for further analysis and characterization. The selected oxPTH-ConforMAB specifically recognized with high affinity all forms of oxidized and misfolded hPTH fragments, but not non-oxidized PTH (aa 1-84).

Example 3 nanoLC-ESI-FT-MS/MS

In order to investigate the oxidation of human PTH(aa 1-84) of example 1 the sample was analyzed directly by high resolution nanoLC-ESI-FT-MS/MS to determine the masses of the whole molecule species and after cleavage by three endoproteases (ArgC, LysC and chymotrypsin) to characterize methionine oxidations at positions 8 and/or 18.

The non-digested human PTH(aa 1-84) and oxPTH(aa 1-84) samples were directly applied to nanoLC-ESI-FT-MS after acidification with 2% formic acid, The digested oxidized human PTH(aa 1-84) samples (1 nmol) were denatured prior digestion by 8 M urea containing 20 mM TCEP (tris[2-carboxyl]-phosphine) reducing agent for 30 min. Iodoacetamide was added to 50 mM final concentration and the mixtures incubated in the dark for another 20 min. After dilution to 0.8 M urea, the samples were digested with ArgC, LysC and chymotrypsin, respectively, in accordance with SOPs of Proteome Factory, Berlin, DE, Enzyme to protein ratio (w/w) was 1:50 in each digest. The acidified peptide digests (ArgC, LysC and chymotrypsin) were pooled and applied to nano-LC-ESI-MS (LTG-FT, Thermo Scientific) analysis using a 35 min nanoLC gradient (Agilent 1100 nanoLC system) with solvent A (0.1% formic acid/5% acetonitrile/94.9% ddH$_2$O) and solvent B (0.1% formic acid/99.9% acetonitrile).

For testing the synthetic oxidized hPTH(1-84) of example 1 was subjected to affinity-chromatography on a column comprising the specific monoclonal oxPTH-conformation antibody (MAB) which binds to an antigenic determinant only present on oxhPTH(aa 1-84) and oxidized hPTH(aa 1-38) polypeptide chains but not on correctly folded hPTH, which antigenic determinant does not encompass methionine sulfoxide or methionine sulfone. No oxidized hPTH(1-84) or fragments thereof were detectable after removal of oxidized PTH molecules In the sample by nanoLC-ESI-FT-MS so that all oxidized PTH forms of the given sample were recognized by the oxPTH-ConforMAB on the immunoaffinity column and quantitatively removed from the flow-through. The mass accuracy was better than 5 ppm for MS data. The MS data were analyzed by MASCOT (Matrixscience) and Qualbrowser (Thermo Scientific) according to the predicted peptide masses. Results are shown in Table 1 and FIGS. 2 and 3.

TABLE 1

Deduced masses of charged peaks in the spectra of non-digested hPTH(aa 1-84)ox and eluate (column-bound oxPTH-fragments)

| MASS [M/Z] | CHARGE Z | MW [DA] | MW INCREASE |
|---|---|---|---|
| 728.16 | 13 | 9453.08 | +32 |
| 729.39 | 13 | 9469.07 | +48 |
| 730.62 | 13 | 9485.06 | +64 |
| 731.85 | 13 | 9501.05 | +80 |
| 780.50 | 12 | 9354.00 | +32 |
| 781.83 | 12 | 9369.96 | +48 |
| 783.17 | 12 | 9386.04 | +64 |
| 788.76 | 12 | 9453.12 | +32 |
| 790.09 | 12 | 9469.08 | +48 |
| 791.42 | 12 | 9485.04 | +64 |
| 792.75 | 12 | 9501.00 | +80 |
| 851.36 | 11 | 9353.96 | +32 |
| 852.82 | 11 | 9370.02 | +48 |
| 854.27 | 11 | 9385.97 | +64 |
| 860.28 | 11 | 9452.08 | +32 |
| 861.73 | 11 | 9468.03 | +48 |
| 863.19 | 11 | 9484.09 | +64 |
| 864.64 | 11 | 9500.04 | +80 |

Figure 2B:
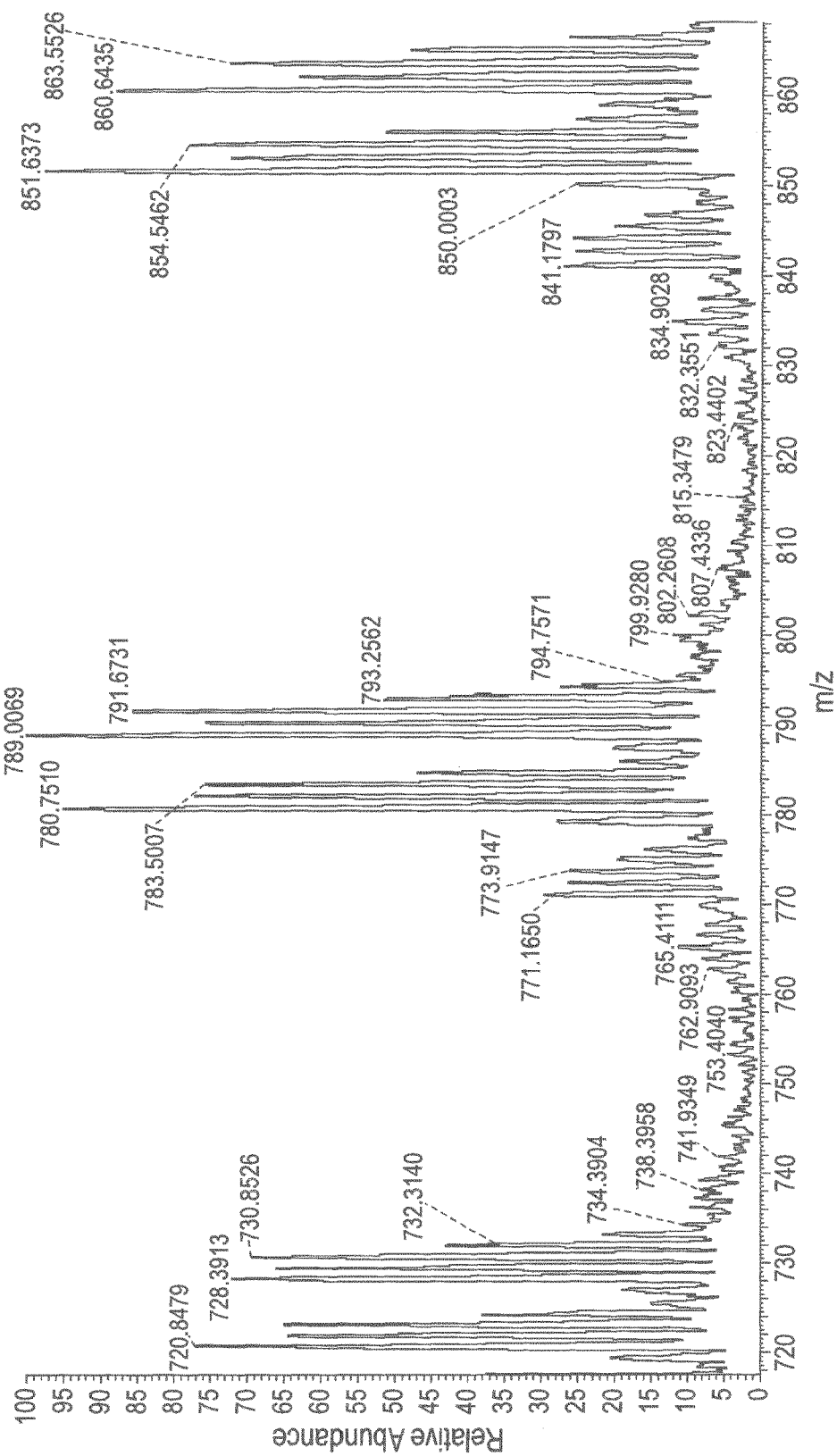
FIG. 2B shows a magnified summed FTMS spectrum for retention time interval 18.30 to 20.50 minutes which spectrum comprises several different charged analyte ions belonging to PTHox and its fragments.
Figure 3A:
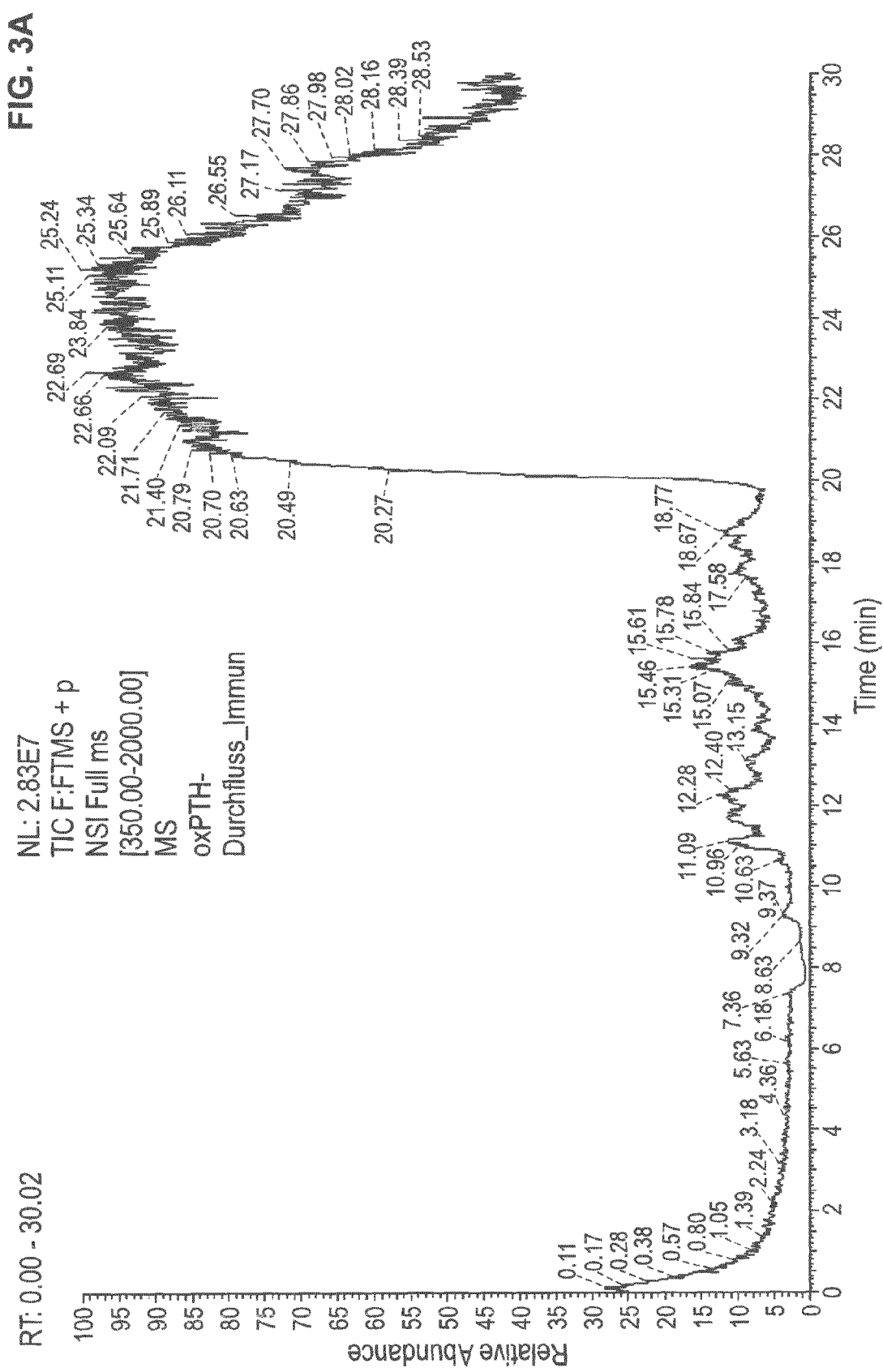
FIG. 3A shows a NanoLC-ESI-FTMS total ion chromatogram of a flow through fraction from the affinity column which binds oxidized synthetic PTH(1-84)ox.
Figure 4A:
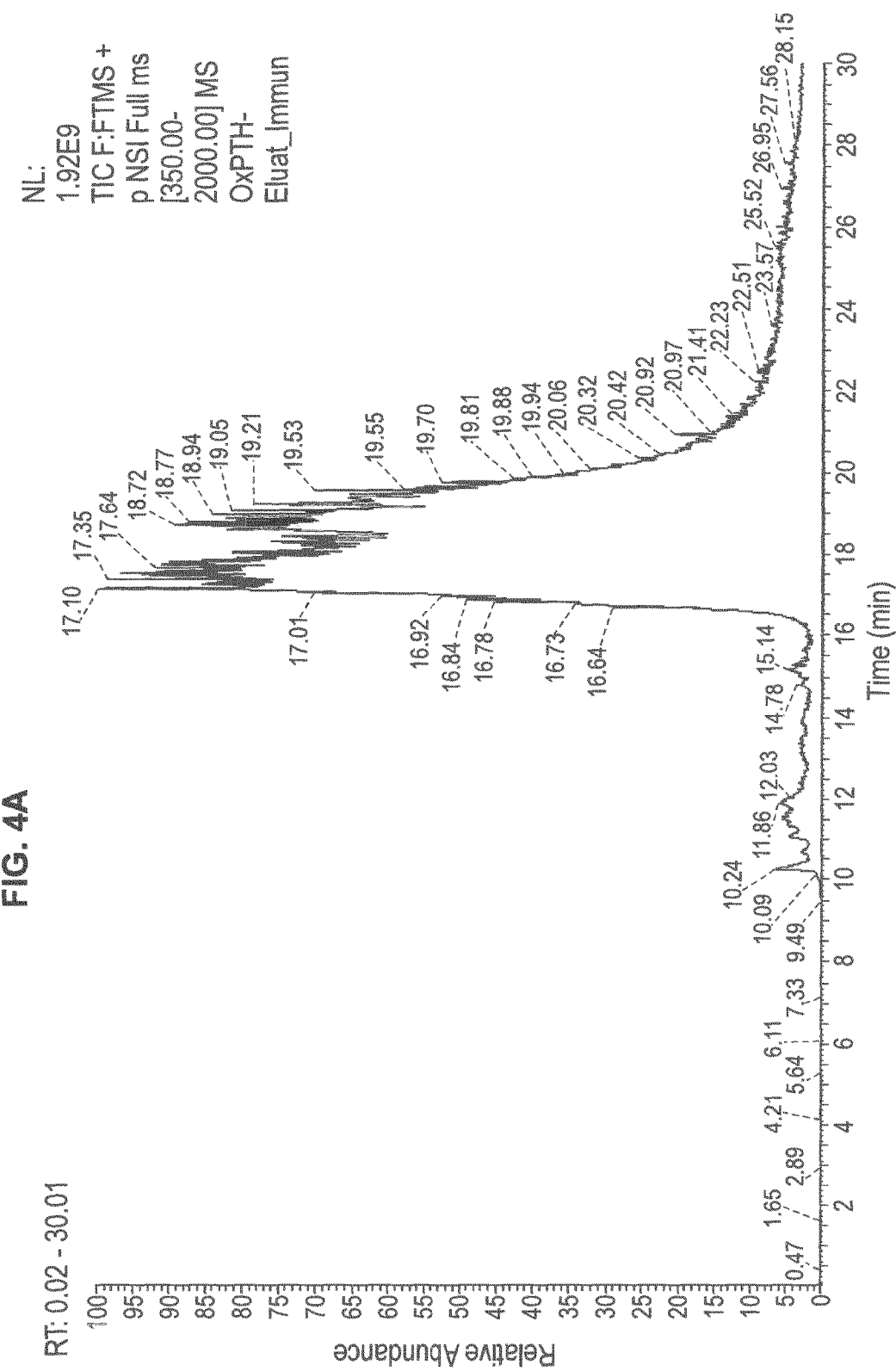
FIG. 4A shows a NanoLC-ESI-FTMS total ion chromatogram of an eluate from the affinity column comprising non-digested oxidized synthetic hPTH(1-84)ox.

No significant mass peaks were observed that can be assigned to any of the hPTH(1-84)ox species by nanoLC-ESI-FT-MS analysis of the flow-through and wash fractions (equilibrating buffer and water) of the column (FIG. 3A.B), whereas several mass peaks corresponding to the different oxidized states of hPTH(1-84)ox were detected in the eluate (FIG. 4A,B; Table 1). Comparison of the spectra of the starting material, non-digested oxidized synthetic hPTH(1-84)ox (FIG. 2B), and the eluate from the affinity column of non-digested oxidized synthetic hPTH(1-84)ox (FIG. 4B) on FIGS. 5A and 5B revealed the same profile despite the difference in peak intensity. The results demonstrate that synthetic oxidized hPTH(1-84) consisted of a considerable variety of products corresponding to the different oxidized methionines. However, the column with the monoclonal antibody (MAB) raised against the oxidized human PTH was specific for all oxidized forms of hPTH(1-84) and removed them all from the probe.

Figure 2A:
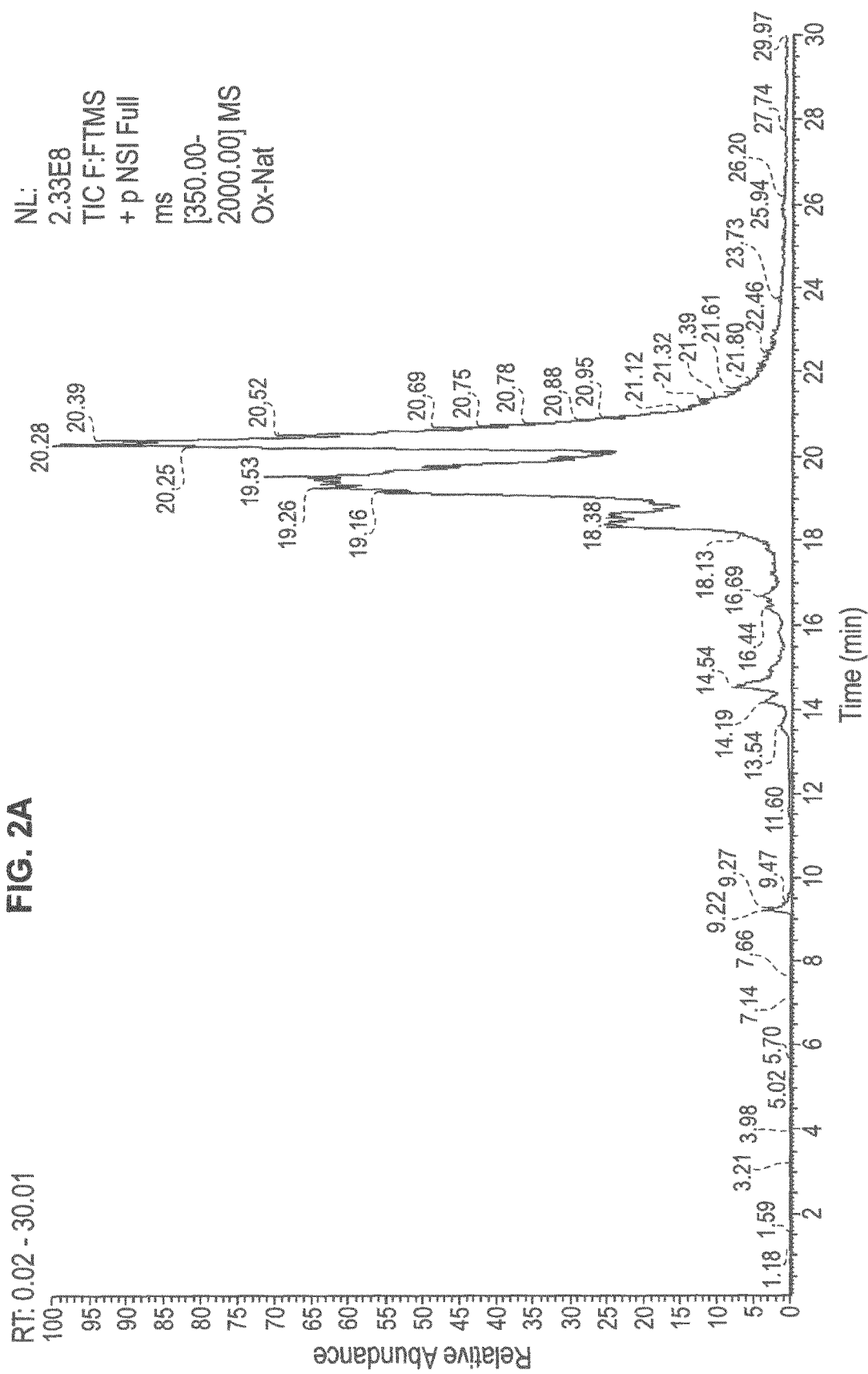
FIG. 2A shows a NanoLC-ESI-FTMS total ion chromatogram of non-digested oxidized synthetic hPTH(1-84)ox.

More precisely, the intact oxidized hPTH(1-84) sample showed TIC-peaks at 18-20 min. The molecular masses corresponded to values shifted by +16, +32, +48, +64 Da caused by methionine oxidation (sulfoxide, +16 Da and sulfone, +32 Da for each residue, and combinations thereof, maximal +64 Da) and by +80 Da for the additional oxidation of tryptophan 23. FIG. 2A shows a NanoLC-ESI-FTMS total ion chromatogram of non-digested oxidized synthetic hPTH (aa 1-84) and FIG. 2B the corresponding magnified summed FTMS spectrum for retention time interval 18.30-20.50 minutes. Several different charged analyte ions have been marked.

Figure 3B:
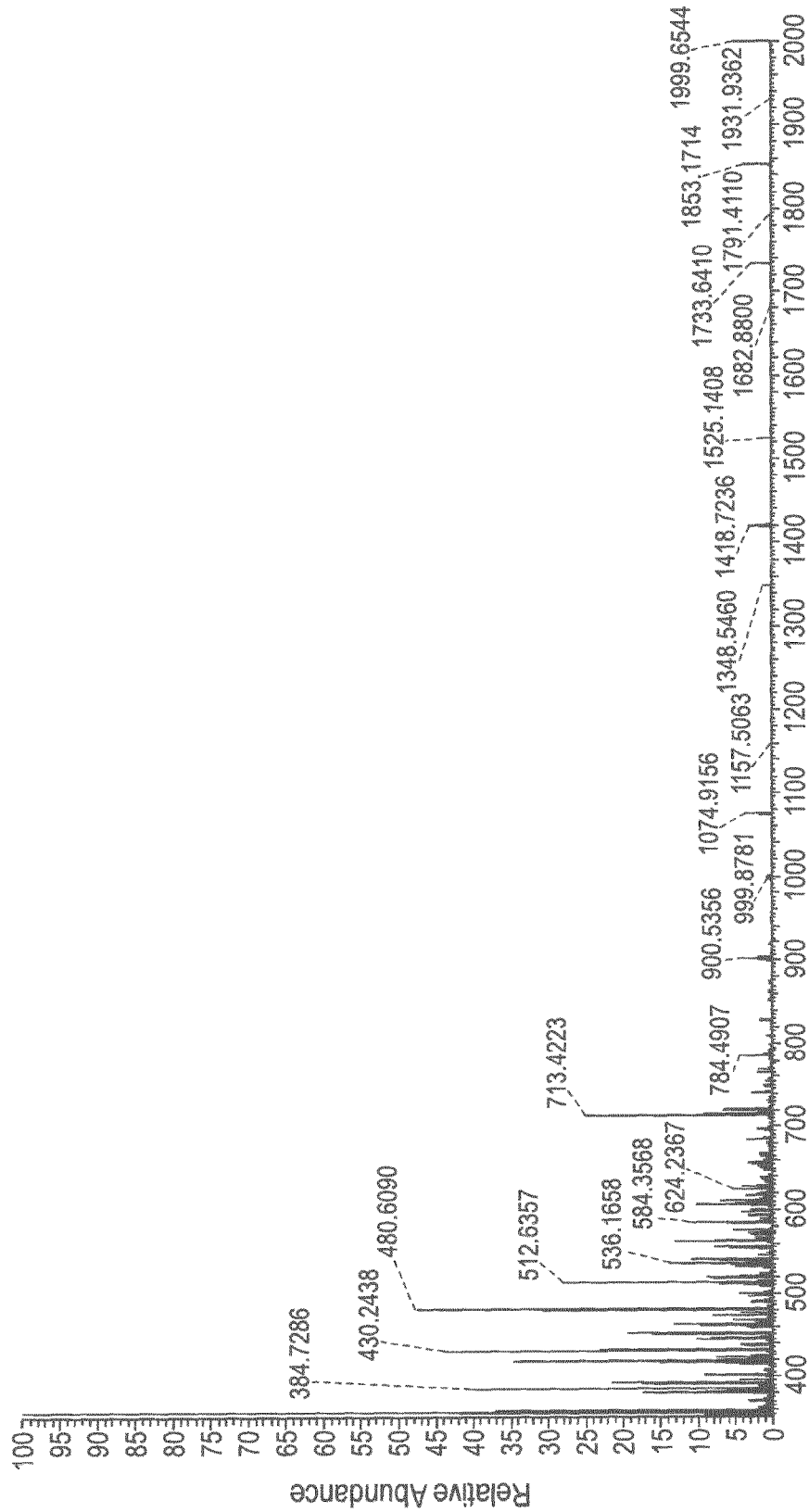
FIG. 3B is a magnified summed FTMS spectrum for retention time interval of 16.50-18.50 minutes which spectrum does not show any analyte masses belonging to PTH or oxidized PTH.

FIG. 3 shows the analysis of the flow through fraction of non-digested oxidized synthetic hPTH(1-84)ox after binding to the immunosorption column. FIG. 3A shows a nanoLC-ESI-FTMS total ion chromatogram of the flow-through and FIG. 3B the corresponding magnified summed FTMS spectrum for retention time interval of 16.50-18.50 minutes. The spectrum does not show any analyte masses belonging to oxidized PTH.

Figure 4B:
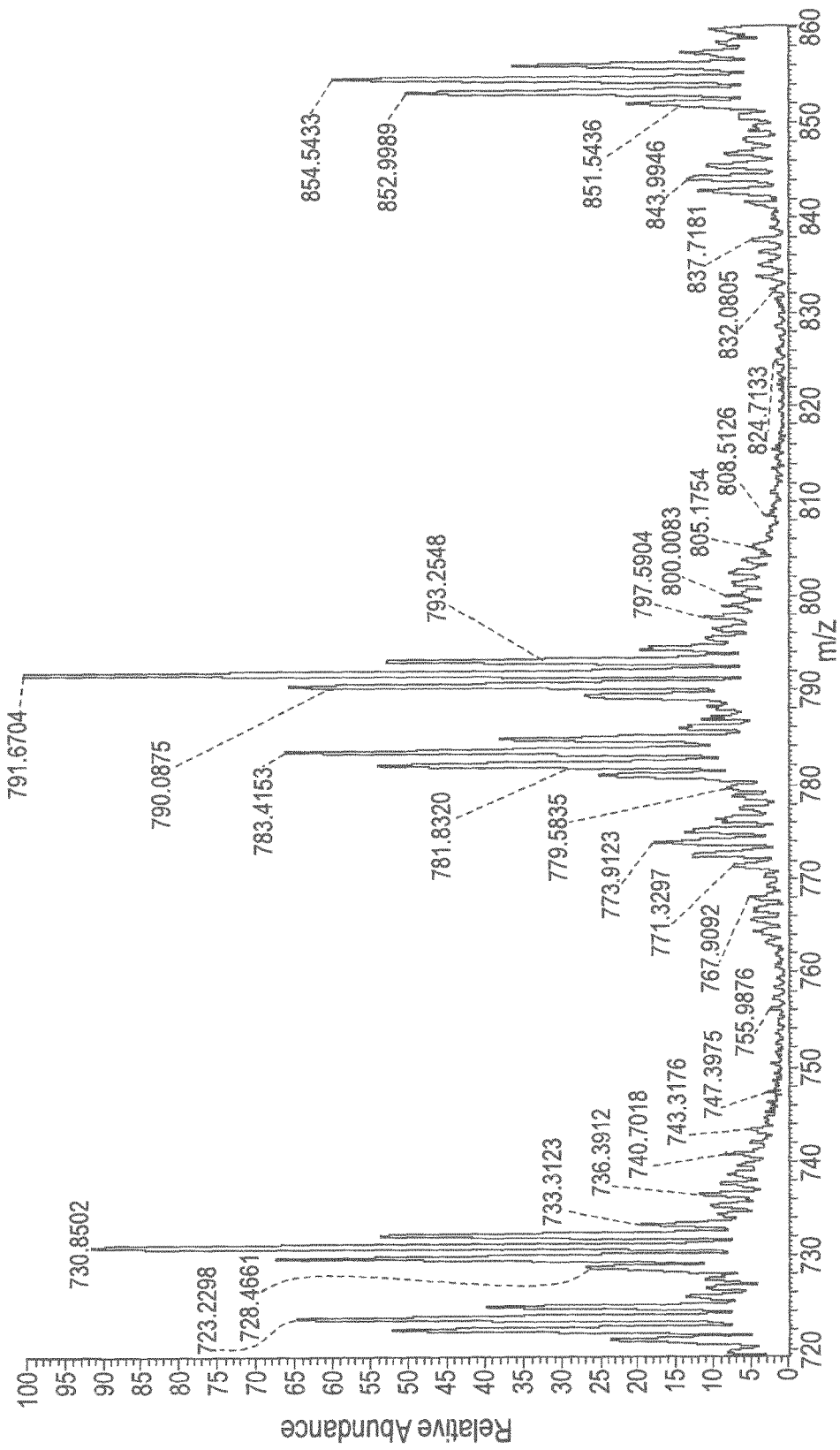
FIG. 4B is a magnified summed FTMS spectrum for retention time interval of 16.50-18.50 minutes comprising several different charged analyte ions of PTH.
Figure 5A:
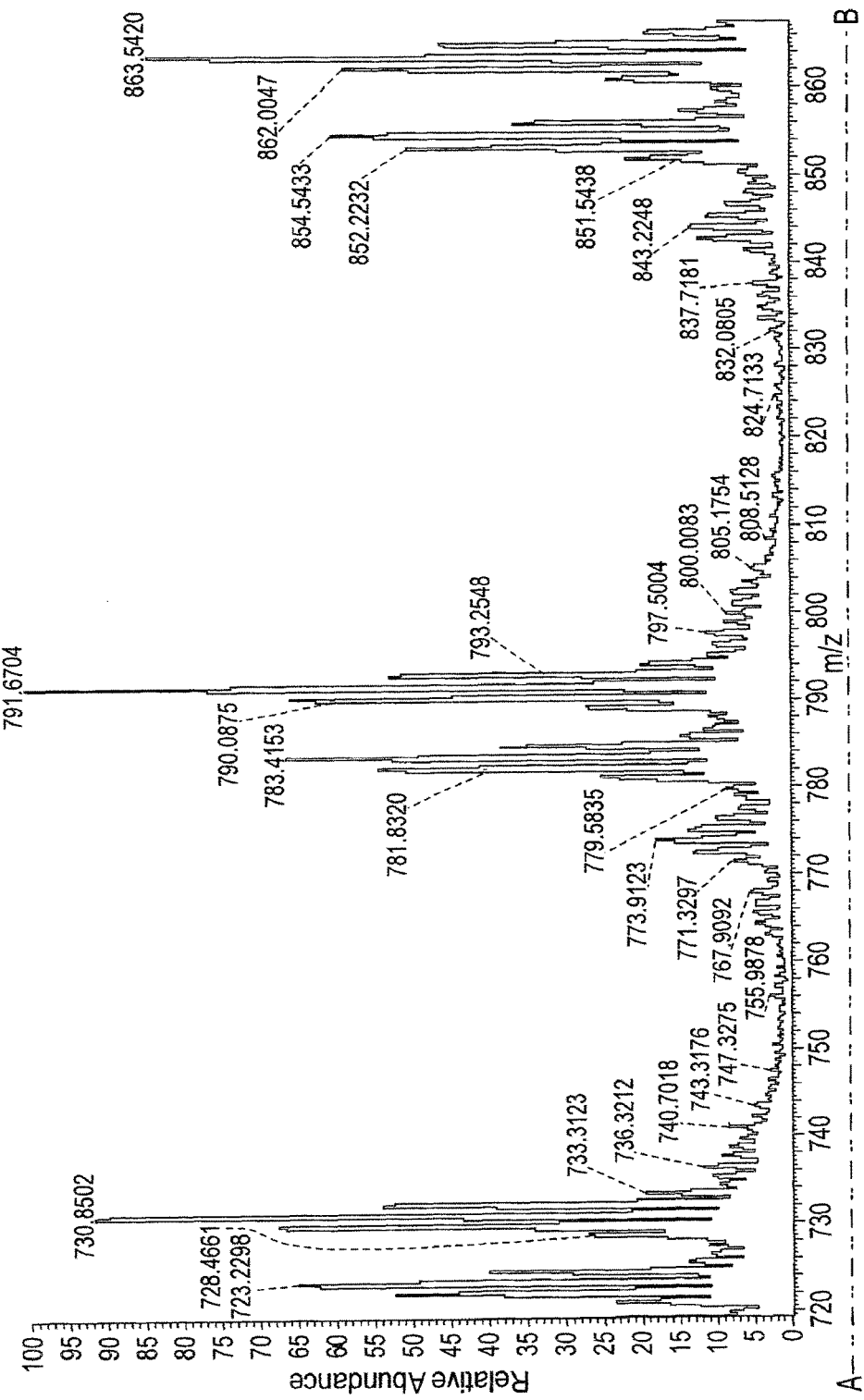
FIGS. 5A and 5B show for comparison the enlarged spectra of the starting material comprising non-digested oxidized synthetic hPTH(1-84)ox (FIG. 1B) and the corresponding eluate after binding to an affinity column (FIG. 3B).
Figure 5B:
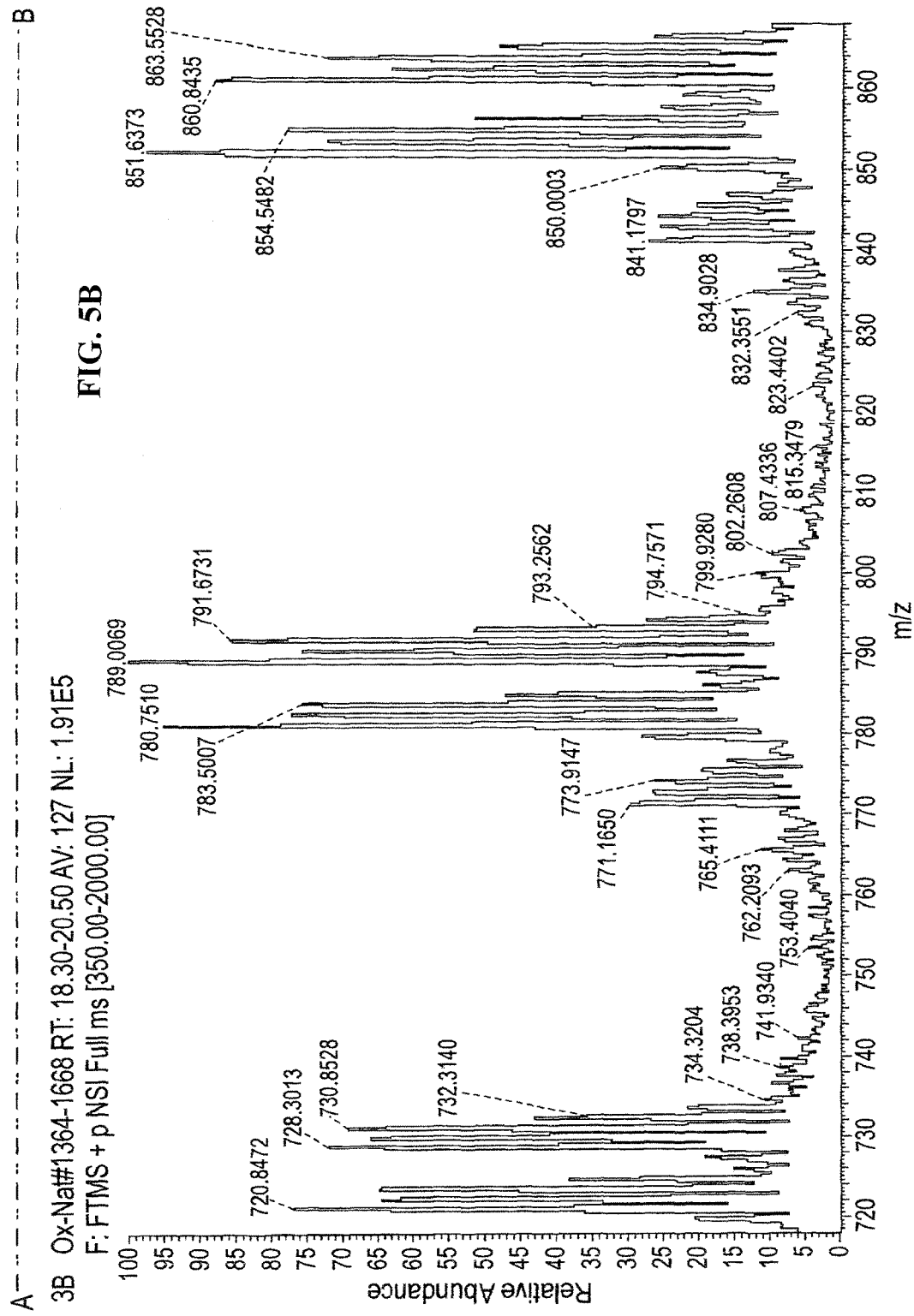

FIG. 4 concerns the eluate from the affinity column of non-digested oxidized hPTH(1-84)ox. FIG. 4A shows the nanoLC-ESI-FTMS total ion chromatogram of the eluate and FIG. 4B again the corresponding magnified summed FTMS spectrum for retention time interval of 16.50-18.50 minutes. Several different charged analyte ions of oxPTH(aa 1-84) were detectable in the eluate, Thus, the examples confirm that all oxidized, misfolded forms of human parathyroid hormone and fragments thereof had a characteristic conformation epitope which can be used for removal of these fragments from a sample for determination of the biologically active concentration of parathyroid hormone.

Example 4

We studied specimens from 18 patients on intermittent haemodialysis treated in our dialysis unit. Specimens (EDTA-whole blood) were taken before start of the dialysis session, centrifuged and immediately stored at −80° C. until further analysis after obtaining of plasma. The study was approved by the local hospital ethical committee. Written informed consent was obtained in each case. Patient's characteristics were obtained from patients clinical records. Serum phosphorus, calcium and C-reactive protein (CrP) were analyzed on an automatic analyzer of the clinical laboratory of the university hospital Charité.

The intact-PTH electrochemiluminescence immunoassay (ECLIA; Roche PTH, Intact [iPTH]) was used for measuring the PTH concentration. The intact-PTH ECLIA of Roche uses a biotinylated monoclonal antibody, which reacts with amino acids 26-32, and a capture ruthenium-complexed monoclonal antibody, which reacts with amino acids 55-64. The determinations were performed on Roche Modular E 170®. The intraassay CV was 4.1% and the interassay CV was 5.8% at concentrations of 35.0 and 180.0 ng/L, respectively.

Human samples were either measured directly (named iPTH in Table 2) or after removal of oxidized PTH by a column which removes oxidized PTH using the selected monoclonal oxPTH conformation antibody described in example 2 which recognizes all forms of oxidized PTH and oxidized PTH fragments. More precisely, the oxPTH-ConforMAB binding column was used with samples from 18 patients on dialysis followed by a classical sandwich PTH ECLIA as it is used in daily clinical practice.

TABLE 2

| PATIENT NO | RENAL DISEASE | AGE YEARS | TIME ON DIALYSIS (YEARS) | SEX | IPTH (NG/L) | REAL IPTH (NG/L) | ox-iPTH (ng/L) | RATIO IPTH/REAL-IPTH | TOTAL CA (MMOL/L) | P (MMOL/L) | CRP (MG/DL) |
|---|---|---|---|---|---|---|---|---|---|---|---|
| 1 | Hypertensive Nephropathy | 62 | 0.3 | m | 43.63 | 8.9 | 34.73 | 0.204 | 2.58 | 1.24 | 0.43 |
| 2 | Diabetic Nephropathy | 73 | 4.0 | m | 796.2 | 70.62 | 725.6 | 0.089 | 2.2 | 2.15 | — |
| 3 | Unknown | 37 | 0.1 | m | 52.84 | 10.35 | 42.49 | 0.196 | 2.53 | 0.81 | 0.03 |
| 4 | Diabetic Nephropathy | 68 | 2.1 | f | 70.8 | 11.18 | 59.62 | 0.158 | 2.23 | 0.91 | 4.08 |

TABLE 2-continued

| PATIENT NO | RENAL DISEASE | AGE YEARS | TIME ON DIALYSIS (YEARS) | SEX | IPTH (NG/L) | REAL IPTH (NG/L) | ox-iPTH (ng/L) | RATIO IPTH/ REAL-IPTH | TOTAL CA (MMOL/L) | P (MMOL/L) | CRP (MG/DL) |
|---|---|---|---|---|---|---|---|---|---|---|---|
| 5 | Acute Kidney Injury | 64 | 0 | m | 46.49 | 9.45 | 37.04 | 0.203 | 2.17 | 1.32 | 3.26 |
| 6 | Diabetic Nephropathy | 63 | 1.6 | f | 42.13 | 5.37 | 36.76 | 0.127 | 2.08 | 1.43 | 12.2 |
| 7 | ADPKD | 70 | 3.3 | f | 1029.00 | 74.76 | 954.2 | 0.073 | 2.1 | 1.37 | 0.53 |
| 8 | Cardio-Renal-Syndrom | 70 | 3.4 | m | 240.4 | 41.89 | 198.5 | 0.174 | 2.38 | 1.57 | 0.32 |
| 9 | Unknown | 70 | 9.0 | m | 105.00 | 18.48 | 86.52 | 0.176 | 2.26 | 1.5 | 3.12 |
| 10 | Diabetic Nephropathy | 65 | 7.0 | m | 1301.00 | 445.30 | 855.7 | 0.342 | 2.53 | 2.23 | 1.74 |
| 11 | Membraneous GN | 45 | 5.4 | f | 311.80 | 24.44 | 287.4 | 0.078 | 1.57 | 2.06 | 0.52 |
| 12 | Membranoproliferative GN (Typ1) | 52 | 1.5 | m | 144.10 | 19.24 | 124.9 | 0.134 | 1.87 | 0.73 | 0.17 |
| 13 | Hypertensive Nephropathy | 61 | 4.1 | m | 73.45 | 15.92 | 57.53 | 0.217 | 2.15 | 2.35 | 0.67 |
| 14 | ADPKD | 57 | 1.2 | m | 281.9 | 44.02 | 237.9 | 0.156 | 2.18 | 1.35 | 13.4 |
| 15 | Diabetic Nephropathy | 73 | 4.0 | m | 116.9 | 19.73 | 97.17 | 0.169 | 2.38 | 1.66 | 4 |
| 16 | Mesangioproliferative GN | 69 | 8.1 | m | 70.81 | 18.51 | 52.3 | 0.261 | 2.62 | 2.28 | 6.7 |
| 17 | Interstitial Nephritis | 61 | 2.6 | f | 76.28 | 11.21 | 65.07 | 0.147 | 2.21 | 1.61 | 2.9 |
| 18 | Unknown | 56 | 10.6 | m | 487.1 | 76.12 | 411 | 0.156 | 2.35 | 2.41 | 0.17 |

For sample preparation, 100 µl aliquots of the slurry with immobilized monoclonal oxPTH conformation antibody (oxPTH-ConforMAB) were filled in MobiSpin-columns equilibrated with PBS buffer, pH 7.4. Then 500 µl of each sample were applied on the column, respectively. The columns were incubated mixing end-over-end for 2 h at room temperature, washed with 250 µl of 0.1 M ammonium acetate buffer pH 7.0, followed by a wash with 250 µl of 0.1 M ammonium acetate buffer pH 7.0, containing 20% acetonitrile, and then eluted twice with 200 µl of elution buffer (0.05 M formic acid, pH 3.5). Flow-through, wash fractions as well as eluate of the column were separately collected and lyophilized. The samples were reconstituted in 500 µl of PBS buffer, pH 7.4 and aliquots analyzed by the intact-PTH ECLIA of Roche (Elecsys® PTH, Intact assay, Roche, Penzberg, Germany). Table 2 shows the basic clinical characteristics and laboratory data of the studied patients on dialysis as well as concentrations of directly measured iPTH (ng/L) and after removal of misfolded, oxidized PTH (real iPTH).

Figure 6:
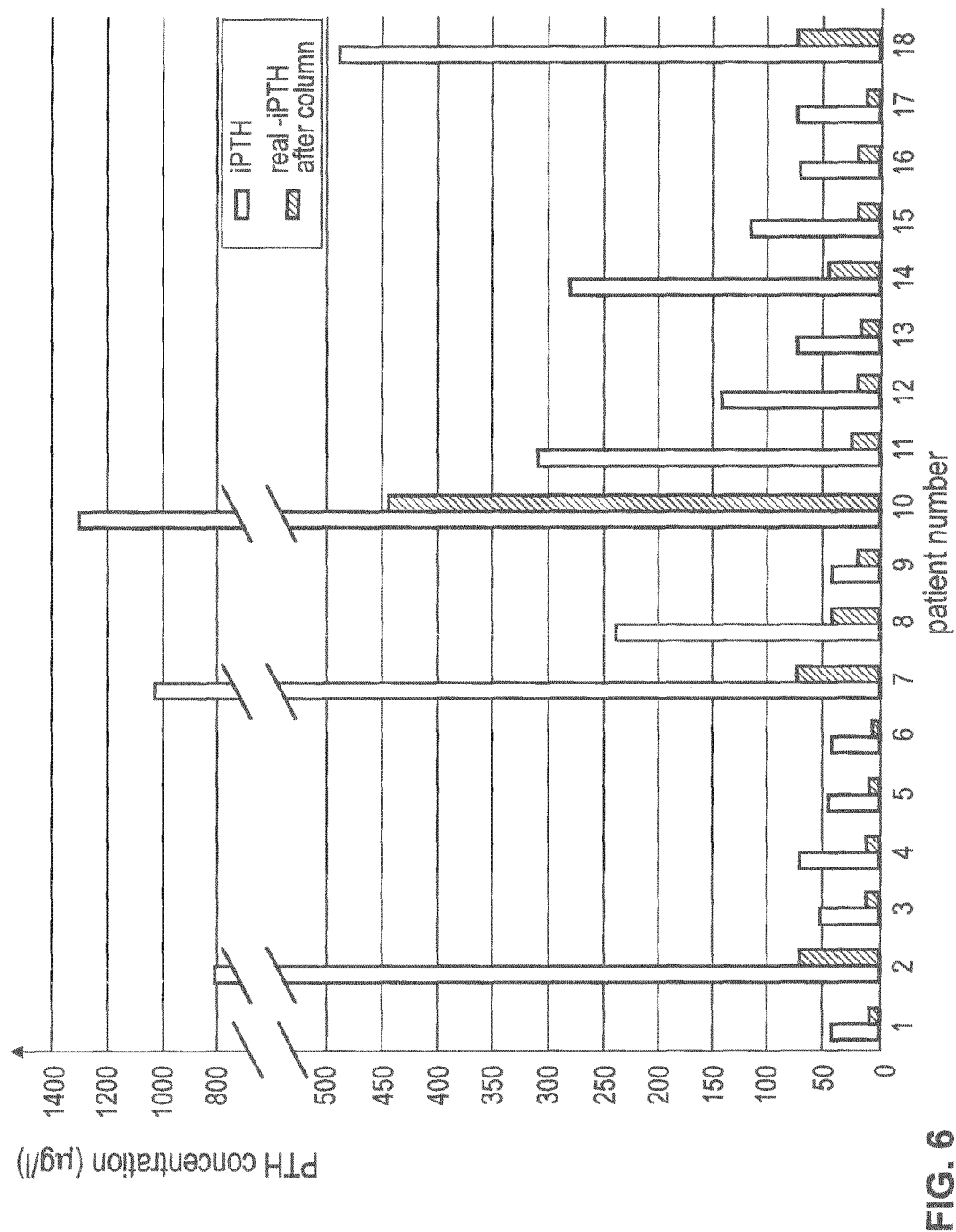
FIG. 6 is a bar diagram comparing directly determined "intact PTH values" in serum of patients on dialysis (blue bars), for further detail see also Table 2, and after removal of misfolded and oxidized PTH peptides from the sample.

The results have been summarized in FIG. 6. Dark (blue) bars show PTH concentrations in serum directly determined by a conventional intact-PTH ELCIA of Roche. When oxidized forms of PTH were removed from the sample, the measured PTH concentrations were completely different (grey/red bars). While the measured PTH concentrations were substantially lower after immunosorption and removal of oxidized PTH forms the relationship between directly measured PTH concentrations and PTH concentrations after removal of oxidized PTH forms varied highly with patients. In some patients only 7% of directly measured PTH was free of oxidation and misfolding, whereas in other patients 34% of the directly measured PTH was intact PTH. Thus, the data show a surprising variation of oxidized to biologically active parathyroid hormone in our patients, possibly in accordance with exposed oxidative stress among the studied patients, the amount of ROS present, the activity of the methionine sulfo reductase type A or the reductive potential in blood and circulation.

Controls

For determining recovery, in a separate series of measurements 500 µl of each sample was spiked with 1 ng of oxidized hPTH (aa 1-84) of example 1. The spiked samples were treated as described in the sample preparation part. The spiking had no impact on the measured PTH value when oxidized PTH and fragments thereof were removed as described. The recovery of added oxidized PTH (aa 1-84) was in the range from 65 to 105%, if directly determined by the iPTH ECLIA.

In order to be sure that the oxPTH columns remove specifically oxidized PTH only, we analyzed some samples after purification with a column able to bind 1,25-dihydroxyvitamin D3. More precisely, we subjected serum samples affinity columns comprising a monoclonal antibody binding to 1.25-dihydroxy vitamin D3 (Art. No. K1107-737, Immundiagnostik AG, Bensheim, DE). A treatment with such a column had little impact on the measured PTH concentration as shown by Table 3.

TABLE 3

| IPTH NG/L | IPTH POST VIT. D COLUMN (NG/L) | RATIO |
|---|---|---|
| 43.63 | 32.43 | 0.74 |
| 796.2 | 684.83 | 0.86 |
| 52.84 | 47.45 | 0.89 |
| 46.49 | 41.86 | 0.90 |
| 70.6 | 61.99 | 0.87 |

The data of Table 3 show that the non-specific binding of PTH accounted roughly for 14% for an immunosorption column comprising a non-specific antibody. Moreover, the non-specific binding of PTH was in all samples about the same so that the affinity column on its own did not significantly influence PTH measurements except for a typical loss of recovery. In other words the column on its own did not significantly influence the results.

To rule out that the tested monoclonal oxPTH conformation antibody MAB is released from the column and interferes with the PTH quantification in the IPTH ELICA of Roche, free monoclonal oxPTH conformation antibody (MAB) was added sample from two patients in a final concentration of 1.8 ug MAB per ml. The samples were then analyzed using the iPTH immunoassay. Those samples where only solvent was added had measured iPTH concentrations of 43.63 [ng/L] (patient a) and 796.20 [ng/L] (patient b), respectively. Adding the monoclonal antibodies to the samples did not alter significantly the results. In the samples with antibodies we measured 35.70 [ng/L] (patient a) and 753.20 [ng/L] (patient b). Thus, even if monoclonal antibodies (MAB) against oxidized human PTH are released these antibodies do not significantly interfere with final iPTH quantification.

Clinical Data

The clinical characteristics are shown in Table 2. We included 17 patients on chronic hemodialysis as well as one patient requiring dialysis due to acute renal failure. We analyzed the clinical specimens with the iPTH immunoassay. In all patients the measured PTH concentrations were substantially lower when considering oxidized forms of parathyroid-hormone (see Table 2 and FIG. 6). It is of note, however, that the relationship between PTH concentrations determined directly with the iPTH immunoassay and those concentrations measured after removal of the oxidized PTH forms is not constant, by contrast the relationship varies substantially probably due to the different degree of oxidative stress among the studied patients. In some patients only 7% of traditionally measured PTH were free of oxidation, whereas in another patient 34% of the traditionally measured PTH were real intact PTH. Taken together, without considering oxidation status of PTH the conventionally measured PTH concentrations using a modern sandwich detection system are detected several fold higher as the concentrations when considering oxidation of PTH. The effect of oxidation of PTH is highly variable among these patients requiring dialysis. There is only a very weak correlation between traditionally measured PTH and oxidized PTH.

In some patients we used beside the iPTH immunoassay from Roche also the PTH(1-84) assay system from Roche. We got basically similar results as described above with the iPTH assay system. Without considering oxidation status of PTH, the traditionally measured PTH concentrations were several fold higher as compared to the concentrations which take due account of the oxidation of PTH.

Figure 1B:
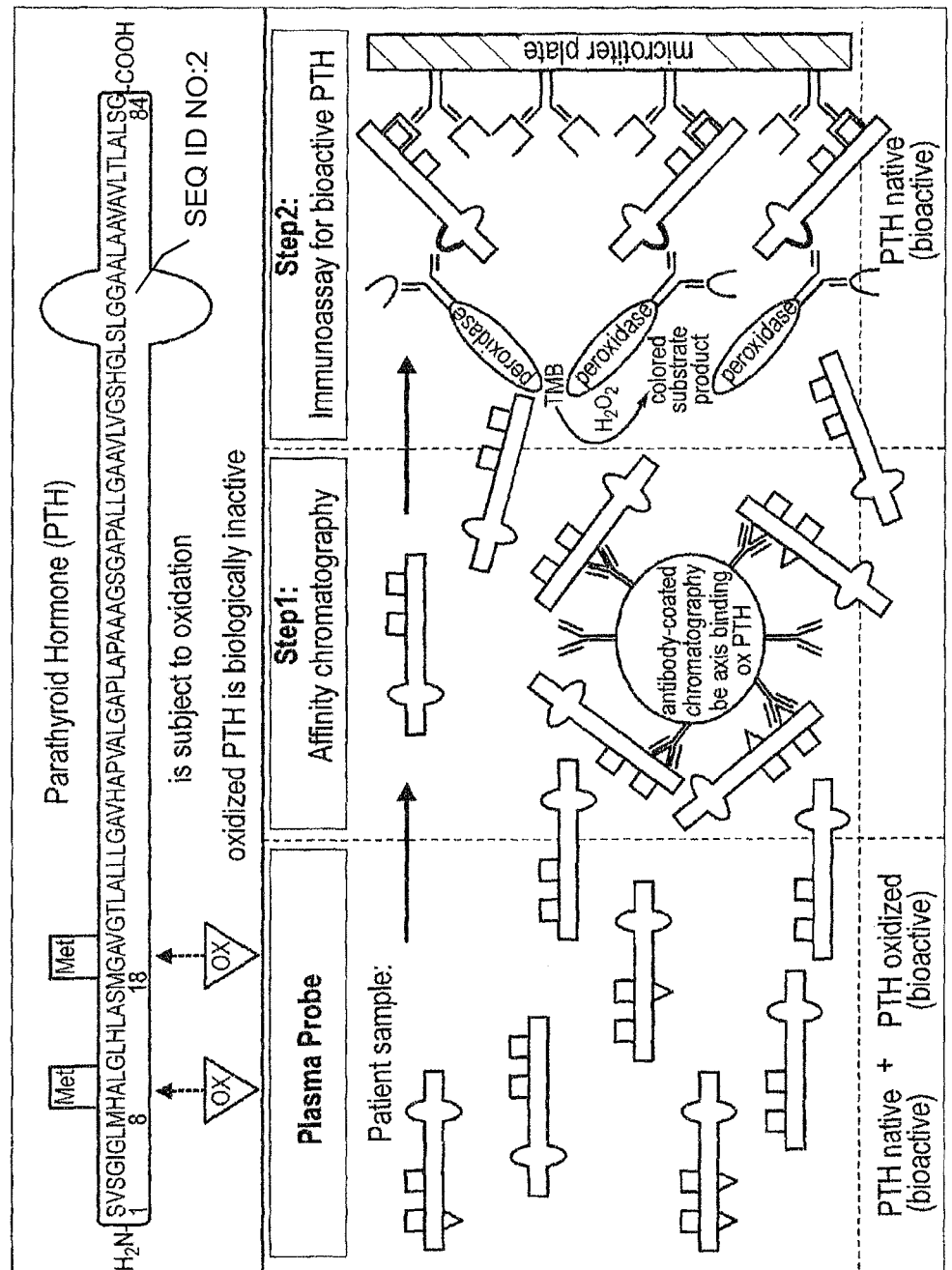
FIG. 1B shows a schematic representation of the new method for measuring parathyroid hormone in human samples. The amino acid sequence SVSGIGLMHALGL-HLASMGAVGTLALLLGAVHAPVALGAPLAPAAAGS-GAPAL LGAAVLVGSHGLSLGGAALAAVAVLTLALSG (SEQ ID NO:2) is shown in the figure.

Using very sensitive mass spectroscopy approaches, the current study demonstrated that oxidation of human PTH (1-84) results in the formation of a variety of products corresponding to the different oxidized methionine resides at position 8 and/or 18 within the parathyroid hormone. A column with the monoclonal antibody (MAB) raised against the hPTH(1-34)ox fragment is specific for all oxidized forms of hPTH(1-84) and removed them all from the sample. The clinical part of our study demonstrated that without considering oxidation status of PTH, the traditionally measured PTH concentrations based on current gold standard methods resulted in much higher PTH concentrations in the clinical samples as compared to the concentrations when considering oxidation of PTH. The effect of PTH oxidation is highly variable among the patients requiring dialysis. There is only a very weak correlation between traditionally measured PTH and PTH data considering the oxidation of this hormone. Given the fact that oxidized PTH (FIG. 1) does not stimulate the PTH receptor anymore to generate cAMP, and is thus most likely biological inactive, clinical strategies for the treatment of hyperparathyroidism in dialysis patients based on measurements of PTH using classical third generation sandwich ELISA techniques are most likely prone to incorrect decision making.

It is known for example that in uremic patients highly specific assays have measured a 2.52, 5-fold increase in the non-suppressible fraction of PTH compared with healthy subjects. Moreover, PTH concentrations measured in uremic serum apparently overestimated PTH-related bone abnormalities also by a factor of 2-2.5. It was suggested that in patients with chronic renal failure, the presence of high circulating levels of non-1-84 PTH fragments (most likely 7-84 PTH) detected by the second generation assay and the antagonistic effects of 7-84 PTH on the biological activity of 1-84 PTH may explain this. However, this hypothesis was never proven in adequately designed clinical studies using for example HPLC coupled to mass spectrometry to really distinguish between different PTH fragments. Our data on the other hand using modern liquid chromatography linked to tandem mass spectroscopy to detect PTH suggest that this well-known overestimation of PTH in patients on dialysis might be most likely due to the presence of oxidized, biologically inactive forms of PTH in patients on dialysis.

Reactive oxygen species (ROS) such as hydrogen peroxide ($H_2O_2$) or hypochlorus acid (HOCl), and free radicals such as hydroxyl radical (OH) or others are continuously formed in vivo. Additional imbalance between formation of ROS and potent antioxidative defence mechanism creates oxidative stress. Uraemia in general is associated with enhanced oxidative stress, and haemodialysis or peritoneal dialysis may in particular contribute to oxidative stress and reduced antioxidant levels in such patients.

One of the preferred highly sensitive targets for oxidation is methionine. The oxidation product methionine sulfoxide can be reversed by reduction with chemicals or erizymatically, whereas oxidation to the methionine sulfone is biologically irreversible. Oxidation of methionine residues can lead to an activation or inactivation of a functional protein, respectively, and the resulting methionine sulfoxide can be reversed enzymatically by a specific reductase. Methionyl sulfoxide reductase has been found in *E. coli* and in mammalian tissues. Oxidation of methionine and its reversal may serve as a regulator for protein activities. The parathyroid hormone contains two methionine residues in the amino-terminal region (position 8 and 18), responsible for the biological activity of the peptide, accessible to alterations trough oxidation. The secondary structure of the parathyroid hormone seems to be essential for its receptor binding. The methionine residue 8 is important for the folding of the hormone and proves the key role for this residue in the structure of the amino-terminal domain and its biological activity. Thus oxidation of methionine residue 8, producing fundamental chances in secondary structure of PTH, is implicated both in binding and in activation of adenylyl cyclase.

Based on published data and our results, we suggest that methionine residues in different peptide hormones, like human growth hormone, somatomammo-tropin, luteotropin as well as PTH may be subject to oxidation resulting in loss of biological activity or receptor affinity. Methionine oxidation may be a general principle in regulation of hormone activity. However, this hypothesis needs to be proved in detail.

Our new assay system is—for the first time—able to differentiate between oxidized and non-oxidized forms of PTH by removing oxidized PTH fragments with a highly specific antibody able to detect and bind all forms of oxidized PTH. The removal of oxidized forms of PTH can be done either—as it was done in the present study—prior to analysis by a coated column followed by a third generation PTH assays (for assay principle see FIG. 6) or even as an integrative part of a third generation sandwich ELISA system. It should also be feasible to combine our approach with modern techniques like liquid chromatography coupled to tandem mass spectrometry (LC MS/MS) in clinical practice in the near future by immunocapture oxidized PTH fragments prior to LC-MS/MS. This will improve the diagnostic performance of LC-MS/MS PTH approaches.

In conclusion, by means of nanoLOESI-FT-MS we were able to demonstrate that oxidation of human PTH (1-84) resulted in the formation of a variety of products corresponding to the different oxidized methionine residues at position 8 and/or 18 within the parathyroid hormone. We screened for a monoclonal conformation antibody against a common antigenic determinant of oxidized human parathyroid hormone and oxidized fragments thereof and found one specific for all oxidized forms of hPTH(1-84) which allows a removal of oxidized parathyroid hormone and fragments thereof from the serum samples of human patients. We also disclose herein that traditionally measured PTH concentrations based on current gold standard methods, which do not account for the oxidation status of PTH, resulted in much higher PTH concentrations in clinical samples specimens as compared to the concentrations when considering oxidation of PTH. The effect of PTH oxidation is further highly variable among the patients requiring dialysis. Given the impact of vascular calcification in end-stage renal disease patients on morbidity and mortality the present results support that measuring whole PTH without "contamination" of oxidized PTH forms will greatly improve clinical decision making with respect to PTH-related bone and cardiovascular abnormalities.

CONCLUSIONS

Thus, the present application is provides a disclosure of a method of obtaining antibody molecules specific for oxidatively inactivated human parathyroid hormone and circulating fragments thereof, comprising a step of obtaining antibodies against human parathyroid hormone peptide by immunizing a non-human animal with an immunogen comprising as hPTH hapten a hPTH peptide oxidized at positions 8, 18 or both, or a respective fragment thereof, and recovering said antibodies from said non-human animal; a step of selecting or purifying said antibodies from antibody molecules that bind to bioactive human parathyroid hormone peptide under physiological conditions to obtain antibodies that specifically bind oxidized hPTH peptide or respective circulating fragments thereof; a step of selecting or purifying said antibodies specific for oxidized hPTH peptide from antibody molecules binding to an hPTH amino acid sequence (primary protein structure) comprising at positions 8, 18 or both methionine R-sulfoxide, methionine L-sulfoxide or methionine sulfone, to obtain antibody molecules hawing a complementary determining region which specifically binds to a conformational epitope (tertiary protein structure) common to inactive oxidized human parathyroid hormone peptides and circulating fragments thereof.

The antibody molecules may be further purified or selected by a step wherein they are further tested for their binding to a primary hPTH structure comprising an oxidized tryptophan at position 22 or which hPTH structure is lacking the utmost aminoterminal amino acids at positions 1 and 2 or both of the hPTH sequence.

The antibodies subjected to these selection or purification steps may be monoclonal antibodies produced by mouse or rat cell clones. A person skilled in the art will appreciate that the antibodies for screening and selection may also be recombinant antibody molecules or antibody fragments or single-chain antibodies from a synthetic antibody library. If the antibodies are recovered from a non-human animal, the immunogen for eliciting these antibodies is preferably is a carrier protein having bound as hapten any one of synthetic oxidized human parathyroid hormone, synthetic oxidized fragment of human parathyroid hormone or synthetic oxidized peptide comprising the amino acid sequence 1 to 38 of human parathyroid hormone or a substantial portion, fragment or variant thereof, Further preferred embodiments and the scope of the present invention are pointed out in the appending claims.

The invention claimed is:

1. A method for measuring an active parathyroid hormone level in a sample of body fluid comprising the steps of
   (i) screening antibodies that specifically bind inactive human parathyroid hormone (hPTH) peptides and circulating inactive hPTH fragments thereof, the screening comprising
      a) obtaining antibodies against human parathyroid hormone peptide by immunizing a non-human animal with an immunogen comprising as hapten oxidized parathyroid hormone or an oxidized fragment of parathyroid hormone, and recovering said antibodies from said non-human animal;
      b) selecting or purifying said antibodies from antibody molecules that bind to bioactive human parathyroid hormone peptide under physiological conditions to obtain antibodies that specifically recognize oxidized parathyroid hormone or fragments thereof; and
      c) selecting or purifying said antibodies against oxidized parathyroid hormone by their binding to an hPTH amino acid sequence (primary protein structure) comprising at positions 8, 18 or both methionine R-sulfoxide, methionine L-sulfoxide or methionine sulfone, to select or obtain antibody molecules having a CDR that specifically binds to a conformational epitope (tertiary protein structure) of oxidized or inactive human parathyroid hormone peptides;
   (ii) contacting the sample with a solid phase or slurry to which are bound said screened antibodies, and
   (iii) measuring the concentration of parathyroid hormone in the sample for determining the level of active hPTH.

2. The method of claim 1, comprising a further selecting or purifying of said antibody molecules by their binding to a conformational epitope of hPTH comprising an oxidized tryptophan at position 23 or lacking the utmost aminoterminal amino acids at positions 1 or 2 or both.

3. The method of claim 1, wherein said antibodies are obtained from antibody-producing cell clones, mouse or rat B-cell clones.

4. The method of claim 1, wherein said antibodies are recombinant antibodies, antibody fragments or single-chain antibodies expressed by clones of a synthetic antibody library.

5. The method of claim 1, wherein the immunogen is a carrier protein hawing bound as hapten any one of synthetic oxidized human parathyroid hormone, a synthetic oxidized fragment of human parathyroid hormone or a synthetic oxidized peptide comprising the amino acid sequence 1 to 38 of human parathyroid hormone or a substantial portion, fragment or variant thereof.

6. The method of claim 1, wherein the antibodies are purified or selected by affinity chromatography using fragments of synthetic oxidized hPTH peptide linked to a solid phase or a marker molecule.

7. The method of claim 1, wherein the conformational epitope comprises the amino acid sequence 3 to 34 of the human parathyroid hormone.

8. The method of claim 1, comprising a further measuring the concentration of parathyroid hormone by a two-site immunoassay wherein one of the two antibodies binds in the aminoterminal portion with amino acids 1 to 34 of the parathyroid hormone.

9. The method of in claim 1, comprising a further measuring the concentration of parathyroid hormone fragments by tandem mass spectroscopy.

* * * * *

SEQUENCE LISTING

```
<160> NUMBER OF SEQ ID NOS: 2

<210> SEQ ID NO 1
<211> LENGTH: 115
<212> TYPE: PRT
<213> ORGANISM: Homo sapiens

<400> SEQUENCE: 1

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 2
```

```
<211> LENGTH: 84
<212> TYPE: PRT
<213> ORGANISM: Homo sapiens

<400> SEQUENCE: 2

Ser Val Ser Gly Ile Gly Leu Met His Ala Leu Gly Leu His Leu Ala
1               5                   10                  15

Ser Met Gly Ala Val Gly Thr Leu Ala Leu Leu Leu Gly Ala Val His
                20                  25                  30

Ala Pro Val Ala Leu Gly Ala Pro Leu Ala Pro Ala Ala Ala Gly Ser
            35                  40                  45

Gly Ala Pro Ala Leu Leu Gly Ala Ala Val Leu Val Gly Ser His Gly
        50                  55                  60

Leu Ser Leu Gly Gly Ala Ala Leu Ala Ala Val Ala Val Leu Thr Leu
65                  70                  75                  80

Ala Leu Ser Gly
```